United States Patent [19]

Williams

[11] 3,996,937

[45] Dec. 14, 1976

[54] CLAMP FOR ANATOMICAL TUBES

[76] Inventor: Robert W. Williams, 3201 S. Maryland Parkway, Las Vegas, Nev. 89109

[22] Filed: Feb. 3, 1975

[21] Appl. No.: 546,209

[52] U.S. Cl. ............................ 128/325; 24/261 R; 128/346

[51] Int. Cl.² .................. A61B 17/12; A61B 17/08

[58] Field of Search .......... 24/261 R; 128/325, 346

[56] References Cited

UNITED STATES PATENTS

| 243,629 | 6/1881 | Sanderson | 24/261 R UX |
|---|---|---|---|
| 1,236,282 | 8/1917 | Fontaine | 24/261 R X |
| 2,250,605 | 7/1941 | Rubin | 128/346 |
| 3,586,002 | 6/1971 | Wood | 128/346 X |
| 3,608,554 | 9/1971 | McGuinness et al. | 128/346 X |
| 3,866,611 | 2/1975 | Baumrucker | 128/346 |

Primary Examiner—Channing L. Pace
Attorney, Agent, or Firm—Jerry R. Seiler

[57] ABSTRACT

A clamp of the disposable or reusable type for anatomical tubes comprises at least three evenly spaced elongated and parallel clamp members all lying along a substantially single plane when the clamp is closed and which members are normally biased to a closed condition. In a preferred embodiment, the device comprises a single length of spring wire or rod formed to provide the clamp members and handle means for opening the clamp.

21 Claims, 5 Drawing Figures

CLAMP FOR ANATOMICAL TUBES

BACKGROUND OF THE INVENTION

Anatomical tube clamps and especially clamps for blood vessels have been designed with the intent of achieving satisfactory occlusion of the vessel while preventing flow of the anatomical secretion within the tube, thus minimizing trauma or injury to facilitate surgical repair. Although it is most desirable to avoid injury to the walls of any anatomical tube such as bowels, ureters, etc, it is especially important when occluding blood vessels which nourish vital life support structures during surgery and microsurgery. Such small vessels which may have diameters as small as about one millimeter have vessel walls which are quite fragile and are easily susceptible to injury especially where exposed to sharp or irregular surfaces or edges. In many cases, where clamps or clips are secured on a vessel, even slight movement of the device may stretch, scrape, or abrade the vessel which, even though not enough to cause rupturing, will damage the vessel wall to such an extent that clotting of the vessel or later deterioration may occur. Other known clamps occlude by squeezing the vessel between opposing and converging surfaces which may result in a pinching or a crushing injury directly to the vessel wall.

In dealing with the surgically treatable diseases of the brain or heart for example, the blood supply to critical anatomical areas is often supplied by blood vessels with diameters in the range of one millimeter. Blood vessel walls of all sizes are extremely fragile and traumatic injury to those structures by any present occlusive device, will often lead to fragmentation of the smooth anatomical cell layers of the wall with resulting spontaneous blood clotting, (thrombosis) and ultimate death of the structure nourished by the vessel. The histological damage leading to cell destruction and deterioration in any anatomical tube which is clamped by present surgical devices may occur due to exposure to sharp or irregular occluding surfaces, stretching of the tube beyond viability, a direct squeezing of the tissue by opposing surfaces (pinching), or an interruption of the microscopic vessels carrying blood to the wall of the anatomical tube itself which are necessary for the nutrition and viability of cell layers comprising the wall of the anatomical tube.

SUMMARY OF THE INVENTION

It is an object of the present invention to provide a simple and yet effective clamp for occluding anatomical tubes, especially blood vessels, and more especially those blood vessels of the micro-vascular size (1 millimeter and less). It is also the object of the invention to provide a disposable or reusable clamp which can be easily applied to vessels and moved thereon without affecting or altering the occlusion while avoiding any injury to the walls of such tubes. It is still another object of the invention to provide an occluding mechanism which is substantially uniform at the contact surface and without sharp or abrupt edges, without direct squeezing or pinching features which would directly traumatize the cell layers of the tube or interrupt the nutritional blood supply to the cells of the wall of the anatomical tube itself. It is yet another object of the invention to provide a device which will occlude any surgically treatable blood vessel in such a manner as to avoid trapping blood within the occluded area which will spontaneously clot, and at the same time avoid significant pinching, squeezing, or stretching phenomena in the occluded area which could rupture capillaries within the vessel wall leading ultimately to inflammation, cell breakdown and again, spontaneous blood clotting. It is an additional object of the invention to provide a means for occluding an anatomical tube, and particularly a blood vessel without compression or squeezing the walls by directly opposing surfaces throughout or substantially along the area of occlusion. It is yet another object of the invention to provide an occluding device having automatic stop means for preventing inadvertent stretching or excessive pressure on the walls of the anatomical tube or vessel when the clamp is closed.

The above objects and obviation of problems experienced with clamps known heretofore are achieved with a device of the present invention. The clamp is not only simple in its design and operation but achieves superior occlusion without the danger of direct trauma or other incident no matter how it is placed on the vessel or otherwise inadvertently moved or displaced thereon or removed without opening.

The clamp utilizes a plurality of closure members and preferably three substantially evenly spaced elongated and parallel clamp members, two of the clamp members lying along opposite sides of the third member. In a preferred embodiment a single length of spring or wire is formed to provide the clamp members as well as a pair of handle members, one of which is secured directly to the outside clamp members and the other to the interior third clamp member, and which clamp members are normally biased to the closed position so that compression of the handle members cause the clamp to open. These features as well as other advantages will be more fully explained in the following detailed description.

DETAILED DESCRIPTION OF THE INVENTION

Figure 1:
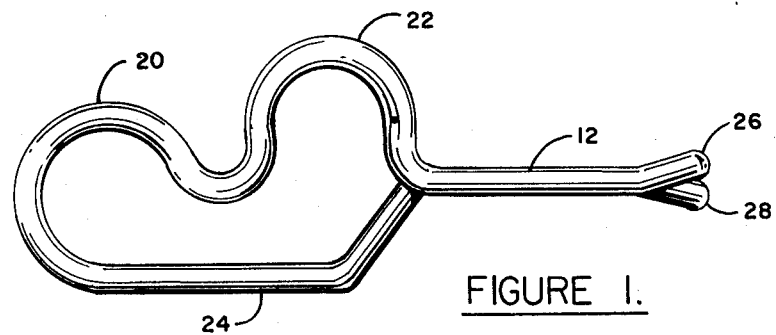
FIG. 1 is a side elevational view of the clamp of the invention in a closed condition.
Figure 2:
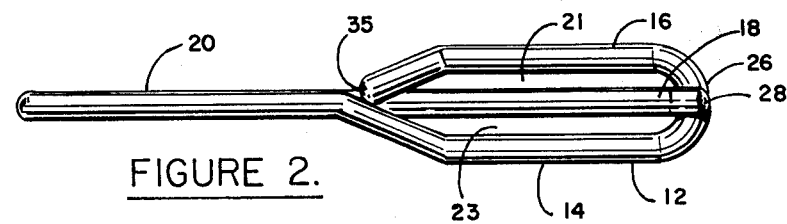
FIG. 2 is a bottom view thereof.

Observing initially FIGS. 1 and 2, there is shown the device in its preferred embodiment in a closed condition as it normally is biased with having a handle portion 20 comprising upper and lowr handle members 22 and 24 which are biased away from one another or spread apart. The shape of the handle members is not especially critical so long as they can either be readily grasped between the fingers for compression or similarly grasped and operated by a delivery means.

Figure 4:
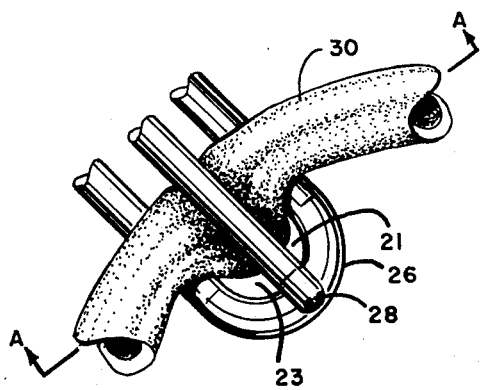
FIG. 4 is a partial perspective view of the clamp in a closed position on a vessel.
Figure 5:
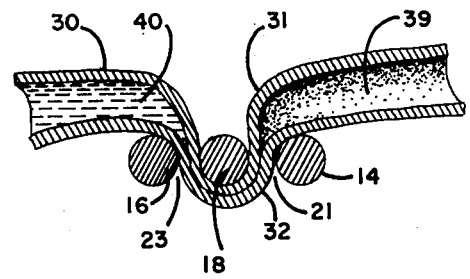
FIG. 5 is a sectional view taken along lines A—A of FIG. 4.

Clamping means 12, in this embodiment, comprises three elongated clamp members 14, 16 and 18. In the closed condition and normal rest position these clamp members are substantially parallel and lie along a single plane especially illustrated in FIG. 1. Moreover, the clamp members are separated uniformly so that spaces 21 and 23 on either side of central clamp member 18 are uniform substantially along the entire length between the interior surfaces of the parallel outside clamp members 14 and 16. The importance and purpose of this uniformity is illustrated in FIGS. 4 and 5 wherein a vessel or other tube occluded in the device of the invention will be uniformly engaged and restricted by the device no matter where it is positioned along the length of the clamp members. With such a feature, the operator need not be concerned as to whether the clamp is placed so that the vessel is disposed too far forwardly or rearwardly along the parallel length of the clamp members since closure of the vessel will be substantially uniform entirely along the vessel-clamp contact surface. Thus, the importance of the three elongated clamp members being parallel in the closed position is to achieve uniform closure of the vessel substantially entirely along the length of the clamp members at the area of contact of the vessel. The length of the clamp members is not critical, so long as the uniformly spaced surfaces extend fully along the collapsed vessel walls being occluded by the device.

In the preferred embodiment, where the device is formed of a single length of spring wire or rod, the two outside clamp members 14 and 16 form and define an elongated cavity between their facing interior walls to receive the third clamp member. These outside members are joined by a U-shaped bridge 26. This feature is clearly illustrated in FIG. 2. Moreover, the bridge is preferably offset angularly from the plane extending along the length of clamp members 14 and 16 as shown in FIG. 1. The purpose for this angular displacement of bridge 26 is to provide an offset stop and self-centering feature when end segment 28 of central clamp member 18 lies in abutment or rests against bridge member 26. Accordingly, it is also preferred that end 28 also be angularly displaced from the plane extending along central clamp member 18 and which angular displacement cooperates with that of bridge 26 so that when these components are in abutment in the closed position shown in FIG. 1, all three of the clamp members lie substantially along a single plane extending along their elongated axis. The angle of the bridge or central clamp member end is not especially critical but those components are preferably at an angle of between about 5° and about 20° from horizontal or the axis along the respective elongated clamp member from which they extend. The bridge may also be provided with a more pronounced means for receiving and maintaining the central clamp member position and concomitantly its precise longitudinal alignment and uniform spacing from the outer clamp members. Such means may be in the form of a notch, groove, slot or other equivalent feature, suitably positioned to achieve the desired result. It is also preferred that end segment 28 of the central clamp member be rounded as shown so as not to present any edges or sharp surfaces which could inadvertently injure or abrade tissue, particularly a vessel on which it has been placed or removed. Thus, even if the forward end of bridge 26 and end 28 contact an additional or secondary anatomical structure, injury is normally avoided.

Figure 3:
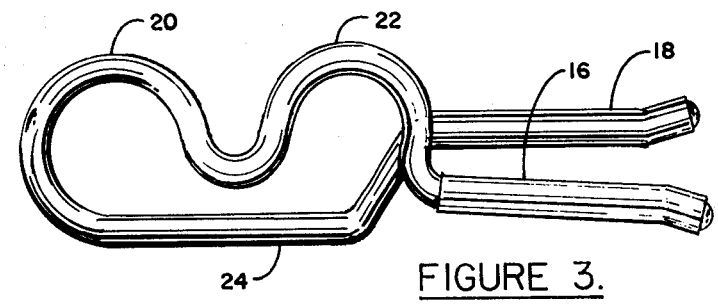
FIG. 3 is a side elevational view of the clamp of FIG. 1 shown in an open condition.

FIG. 3 illustrates opening of the device wherein handle members 22 and 24 are compressed toward one another thereby overcoming the bias of the spring material which normally urges these handle members apart and concomitantly the clamp members in the closed position or condition. Thus, by overcoming the spring bias of the material of which the device is formed the elongated clamp members are open as shown in FIG. 3 in a scissor-like manner whereby central clamp member 18 is urged downwardly and outside clamp members 14 and 16 are urged upwardly to form an opening into which the vessel or tube to be clamped and occluded is received. Once the clamp is in place with the vessel area to be occluded centered between the outside clamp members, the operator simply releases the handle thereby allowing the clamp members to automatically close at which time the vessel will become occluded in a manner shown in FIGS. 4 and 5.

It will be noted in the preferred embodiment shown, that outside clamp member 14 is directly connected to first or upper handle portion 22 while central clamp member 18 is similarly directly connected to second or lower handle portion 24. Other means for achieving the same purpose may be used. Thus, the specific shape or bend of the wire or rod material of which the device is preferably produced may be modified from that illustrated to achieve the same function and purpose. It will also be noted that in the embodiment shown, a single length of wire or rod is formed extending between terminal ends 28 and 35 so that the device is unitary in its preferred construction thereby lending simplicity to its design as well as in production and ease of manufacture.

Observing also FIGS. 4 and 5 there is shown the device in position to occlude vessel 30 which lies over a portion of the surface of each of the outside clamp members 14 and 16 and extends around the opposite surface of central clamp member 18. Occlusion occurs as vessel walls 31 and 32 collapse and are forced toward one another with the interior vessel wall surfaces meeting substantially along the length thereof lying between the facing interior surfaces of the outside clamp members 14 and 16. Moreover, since there are not opposing surfaces squeezing the vessel walls therebetween as is normally found in other types of clamps or clips, there is no danger of the vessel walls being unduly compressed or pinched which could cause damage to the fragile cells and nutritional capillaries in the vessel walls. At the same time, with this occlusion extending substantially and uniformly along the entire area lying between the interior clamp member surfaces, fluid and especially blood is forced therefrom to prevent clotting. Thus, not only is the occlusion and mating of the vessel walls uniform because of parallel disposition of the clamp members and uniform separation therebetween, but prevention of stretching of the vessel is achieved because of the automatic stop feature where terminal end 28 overlies and rest on bridge member 26 as shown in FIGS. 2 and 4. Without such a stop feature, the bias spring effect of the handle could cause the central clamp member 18 to pass entirely through its co-planer disposition with outside clamp members 14 and 16. In addition, because of the cooperating angular displacement of the bridge and central clamp member end, the latter is self centering, even where the clamp is made of relatively thin wire. Moreover, because of these characteristics, if the clamp becomes inadvertently somewhat moved or dislocated either angularly with respect to the vessel or becomes dislocated so that the vessel lies closer to the handle or the opposite ends of the clamp members, there will be substantially no adverse effect on the vessel since the surfaces and spacing between the various clamp member surfaces in which the vessel is received are unchanged and uniform substantially throughout. Even if the clamp is inadvertently pulled off or away from the vessel without being opened, since terminal end 28 and bridge 26 present no sharp surfaces and because of their relative angular displacement, there will be no injury or pinching of the vessel and the clamp need merely be again properly positioned on the vessel for suitable occlusion. Moreover, because of this feature, to remove a clamp, especially where the clamp is being used in a very small area such as during micro-surgical techniques, a delivery system need not be used for removing the clamp and it can simply be pulled away without endangering or stretching the vessel. Additionally, the clamp may be easily repositioned along the length of the vessel without opening the clamp but instead by simply sliding it to the desired position. Accordingly, it will be evident that occlusion of the vessel is not due to the amount of compression of the vessel walls or their being squeezed or pinched to provide the occlusion but instead, is due to the uniform and effective length along which the vessel walls are held against one another by their own elastic quality against a series of non opposing but fixed members.

It has been found that different sized clamps will be more or less effective on different sized collapsible anatomical tubes especially due to the spacial relationship between the clamp members. Preferably, the distance between the facing inner surfaces of the outside and inside clamp members, i.e., distance across each space 21 and 23 is between about one-third and about two times the diameter of one of the clamp members. More preferably, this distance is between about one-half and about equal to the clamp member diameter. However, the proper sized device must also be used for certain vessels so that the distance between the clamp member, i.e., between their interior and opposing surfaces or the distance across spaces 21 and 23 is between about ½ and about 1½½ times the double wall thickness of the vessel being occluded. Where the space is less than the double wall thickness, because of the elasticity of the vessel wall tissue, there will be slight vessel wall stretching as the wall narrows itself to occupy the spaces 21 and 23. Yet, where the space is unduly small or narrow for the vessel, undue stretching may occur. On the other hand where the space is too large and the vessel fits loosely therein, occlusion may not be satisfactory. Thus, preferably this distance between adjacent closure member surfaces is not greater than the thickness of both collapsed vessel walls, and yet is not less than about two-thirds the double collapsed wall thickness. However, the sizing or matching of clamps with vessels is critical to the extent that the distance between these opposing clamp surfaces is small enough to approximate or bring together the walls between the inner surfaces of 14 and 16 as the tube passes around member 18. The passage of the vessel through the path outlined in FIG. 5 allows for expression of the anatomical fluid both proximal and distal to members 16 and 18 resulting in the occlusive effect without allowing pooling and stagnation of the fluid in spaces 21 and 23 thus leading to complications such as clotting (thrombosis) in the case of blood.

The specific type of material used to produce the clamp is critical only in that according to preferred embodiment, it has a spring-like composition with memory whereby the handle portion acts as the spring for automatically biasing the clamp members to the closed position. Preferably, the material used is circular in cross-section substantially along its length or at least along the clamp member surfaces so that no sharp, angulated, or cutting surfaces are exposed and so that no undue stretching due to angulated surfaces occurs. A spring steel wire or rod and especially the surgical or stainless variety may be used for this purpose and since the length of material used in the device is not great, the clamp can be produced relatively inexpensively thereby allowing it to be of a disposable nature if desired. Moreover, the wire or rod may be of non-metalic material such as nylon or other synthetics with memory properties, or may be coated, especially along the clamp members, with a silicone, rubber, or similar synthetic plastic material to reduce or obviate friction and possible vessel wall abrasion. FIG. 3 illustrates a plastic sleeve over the clamp members for that purpose. If the clamp members are so coated, the above description of the relative distances between opposing clamp member surfaces and diameters is to be interpreted as being measured to the outside surface of the coating. Although the description of the preferred embodiment herein has been primarily limited to a device having three clamp members, a larger number of such members may be incorporated thereby giving a larger area of occlusion on the tube or vessel. The only restriction is that the clamp members are to have the features and characteristics as disclosed herein.

On occasion, biological substance such as colloid heprin or other anitcoagulate substances, may be added to the coating material, especially for the clamp member, to more physiologically accommodate an anatomical tube in its occluded environment. Such a composition would further minimize the possibility of blood from the surrounding surgical dissection from clotting or becoming adherent to other surfaces of the clamp thus obscuring vision and preventing the removal of the device without opening. In addition, the coating material may be color coded in relation to the size and strength of the vessel for which the particular clamp is preferably designed. The memory strength of the materials used in manufacture may vary as the size of the vessel on which it is to be used increases, and the need for disposability versus reusability dictate. For example, in occluding larger and more physiologically stronger anatomical tubes, a large, more expensive and structurally stable and reusable device may be more economical for the consumer.

There are occasions in the treatment of disease states concerning anatomical tubes (blood vessel aneurysms, viscus diverticuli), when an occluding device must be left permanently in the living organism. Many blood clamps (aneurysm clamps, vascular or hemostatic clips) have been designed for this purpose utilizing opposing or pinching surfaces. One such device is shown in U.S. Pat. No. 3,827,438. The principal of plurality of closure of this invention, in relation to permanent occlusion of an aneurysm sac, will prevent the presence of sharp abrasive or crushing forces in contact with the parent vessel, which must not be traumatized if it is to remain patent. Because of the unique way in which the closure members of the device of the present invention render occlusion of a vessel, there is little, if any, danger of injury to the parent vessel. Such features make the occlusive device of the present invention unique. Moreover, because of the rounded and angular disposition of end member 26 and bridge 28, occlusive forces are prevented from being applied to structures approximating the vessel not desired in the occlusion. Thus, damage to adjacent and possibly critical anatomical structures not visible to the surgeon during application of this invention, is minimal, if not eliminated.

Finally, this device may be used as an atraumatic holding mechanism for solid anatomical structures (nerves) which have been severed and required reapproximation during surgical repair. At present, such approximating or holding mechanisms often induce additional injury to the physiological structure thus retarding healing. Thus, the advantages of using the instant device because of its unique characteristics and uniform occlusion means, as well as other advantages thereof will be evident to those skilled in the art.

I claim:

1. A clamp for anatomical tubes comprising at least three spaced elongated parallel clamp members with their respective elongated axes all lying along a single plane and having a space between adjacent sides of said members when said clamp is closed on a tube and means for moving at least one of said clamp members for opening said out of said plane clamp.

2. The clamp of claim 1 wherein said opening means is normally biased to close said clamp.

3. The clamp of claim 2 wherein said opening means comprises first and second handle portions.

4. The clamp of claim 3 wherein said clamp members comprise a first clamp portion and a second clamp portion and wherein said opening means is for spreading said first and second clamp portions apart.

5. A clamp of claim 4 wherein said first clamp portion comprises two elongated parallel clamp members defining a space between facing interior surfaces thereof for receiving the second clamp portion and wherein said second clamp portion comprises a third clamp member lying between said two clamp members of said first clamp portion, and evenly spaced therefrom along at least a portion of the length thereof.

6. A clamp of claim 5 wherein one of said handle portions is for moving one of said clamp portions relative to the other clamp portion for opening said clamp.

7. A clamp of claim 6 wherein said handle portions and said clamp members are formed of a single length of material having a memory.

8. A clamp of claim 7 wherein said material is a spring wire or rod.

9. A clamp of claim 7 wherein a bridge extends between said two clamp members of said first clamp portion at the ends thereof.

10. A clamp of claim 9 wherein said bridge is U-shaped.

11. A clamp of claim 10 wherein said third clamp member has an end segment extending over said bridge and resting on said bridge when said clamp is closed.

12. A clamp of claim 11 wherein said bridge and said end segment extend at an angle from the plane of said parallel clamp members said angles being different.

13. A clamp of claim 9 wherein one clamp member of said first clamp portion terminates at one end opposite said bridge and a second clamp member of said first clamp portion joins one of said handle portions and said second clamp portion terminates at one end adjacent said bridge and at the other end joins the other one of said handle portions.

14. A clamp of claim 1 wherein said clamp members each have a circular cross-section.

15. A clamp of claim 14 wherein the ratio of the distance between adjacent clamp member surfaces and the diameter of said clamp members is between about 1:3 and about 2:1.

16. A clamp of claim 1 comprising first and second elongated parallel clamp members defining a space between facing interior surfaces thereof for receiving a third clamp member lying between said first and second clamp members and evenly spaced therefrom along at least a portion of the length thereof.

17. A clamp of claim 16 wherein a bridge extends between said first and second clamp members at the ends thereof.

18. A clamp of claim 17 wherein said third clamp memnber has an ends segment extending over said bridge and resting on said bridge when said clamp is closed.

19. A clamp of claim 5 wherein said clamp members each have a circular cross-section.

20. A method of occluding an elongated anatomical tube comprising placing said tube between three elongated clamp members and directing said members together until they are substantially parallel and the elongated axis of all of the members lies along a single plane with one of the members disposed between the other two members and spaced substantially evenly therebetween along at least a portion of the length thereof.

21. The method of claim 20 wherein said tube is placed between said clamp members with its elongated axis lying generally normal to the elongated axis of said members.

* * * * *